United States Patent

Plant Pat. 3,803

Patented Nov. 11, 1975

3,803

ROSE PLANT—MEIGERIUM VARIETY

Marie-Louise Meilland and Alain A Meilland, Antibes, and Michele Meilland Richardier, Tassin-la-Demi-Lune, France, assignors to The Conard-Pyle Company, West Grove, Pa.

Filed Oct. 24, 1974, Ser. No. 517,819
Claims priority, application Morocco, Jan. 28, 1974, 16,662
Int. Cl. A01h 5/00
U.S. Cl. Plt.—20 1 Claim

ABSTRACT OF THE DISCLOSURE

A new and distinct variety of rose plant of the hybrid tea class, especially for cut flowers origniated by crossing unnamed and unpatented seedlings, and obtaining a rich light vermilion color of its flowers.

SUMMARY OF THE INVENTION

Figures 1, 2, 3, 4, 5, 6, 7, 8, 9, 10, 11, 12, 13, 14:
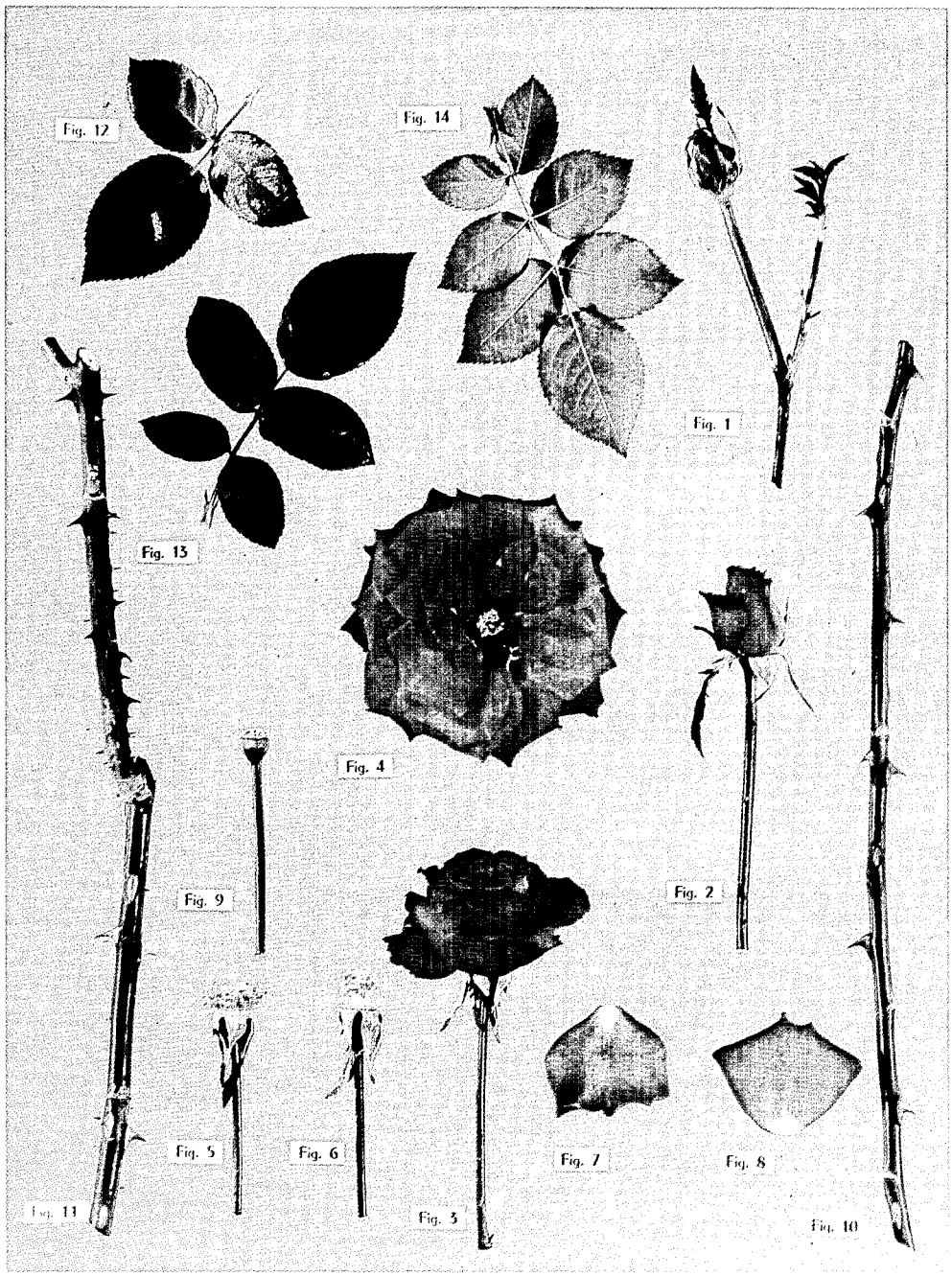

The object of the present invention is a variety of rose-plant of the hybrid tea class, with double vermilion flowers, which is distinguishable from varieties already known in that class and that kind of color, because of the following characteristics:

special aptitude of the plant to winter forcing; and orginality of the rich light vermilion of its flowers.

Because of the characteristics mentioned above, the present invention answers the needs of the horticultural industry, for all uses, and more specially for the production of cut flowers under glass.

The aim that the applicants had in view was to create a variety which would derive the aforementioned advantages from the genetic combination of two genitors whose previous and respective study would allow them to expect, in their common descent, the appearance of the characters sought.

The rose chosen as female genitor was the product of the pollination of the variety MEIalto–219F, more generally known in the trade under the name of Romantica, by the variety Tanorstar; that chosen as male genitor was the product of the pollination of a yet unknown variety born of a crossing made between the variety Show Girl and the variety Meger–561, more generally known in the trade under the name of Baccara (P.P. No. 1,367) and the variety MEIalto–219F, more generally known in the trade under the name of Romantica.

The operation of artificial pollination performed by the applicants can therefore be expressed by the following schematic formula:

$$\left(\frac{\text{MEIalto–219F}}{\text{Romantica}} \times \frac{\text{Tanorstar}}{\text{Super Star}}\right) \times \left(\text{Show Girl} \times \frac{\text{Meger–561}}{\text{Baccara}} \times \frac{\text{MEIalto–219F}}{\text{Romantica}}\right)$$

From the fruits thus formed by this controlled pollination, seeds were extracted whose cells were the results of the combination of factors which existed in the cells of the genitors and in virtue of which these genitors had been precisely chosen.

After having sown these seeds, the applicants obtained 370 small plants, physically and biologically distinct from one another.

After having eliminated all the plants which were deficient or abnormal, or whose characters were too remote from the ones they were seeking, the applicants proceeded with the grafting of the remaining plants, in order to carry on their work exclusively on rose-plants which were, in every respect, in conformity with those produced and commercialized by professional nurserymen.

From then on, they undertook the selective study of the plants thus formed; during which study they were led to eliminate systematically all the rose-plants which had been grafted, with the exceptioin of one only, which was the closest to the desired goal.

This rose-plant grew vigorously and produced easily long stems bearing one flower only, asserting in that way its special aptitude to a production of cut flowers.

Its flowers were, moreover, of a rich vermilion color, of great originality.

Technical tests (grafting inside or outside, with started eye-buds, dormant eye-buds, in heated glasshouses, in cold glasshouses, etc. . . . ) were then made so as to ascertain the behavior of the variety just created.

The results were conclusive and underlined the importance of creating this variety with a view to its industrial exploitation by nurserymen, specially by the producers of cut flowers under glass.

The characters and properties of this new variety, obtained as indicated above, are strictly transmissible by agamic means, also called "asexual," i.e. by any means of vegetative propagation, and in particular by grafting an "eye" which will be called in the trade by the name of Meigerium–0851F and which will be found on industrial plants as well as on cut stems delivered subsequently in the trade. Thus will be obtained once again the rose variety which is the object of the patent, and whose botanical and descriptive characteristics, proceeding from glasshouse-plants, grown in winter at Cap d'Antibes, Alpes-Maritimes, France, are given below.

Asexual reproduction of this new rose by budding at West Grove, Pa., and in France, showed that the characteristics and distinctions come true to form and are established and transmitted through succeeding propagations.

BRIEF DESCRIPTION ON DRAWINGS

The accompanying drawings show as nearly true as it is reasonably possible, to make the same in a color illustration of this character, typical specimen of the flowers and foliage, illustrating in, FIG. 1, a specimen of a young shoot resulting from the development, fairly frequent in this variety, of the 2 or 3 first stipular eyes of a flower-bearing branch, with a specimen of bud at the opening of the sepals;

FIG. 2, a specimen of bud at the opening of the first petals;

FIG. 3, a specimen of a flower during the course of opening;

FIG. 4, a specimen of a fully-open flower, flat view, inside;

FIG. 5, a specimen of receptacle showing the disposition of the stamens;

FIG. 6, a specimen of receptacle showing the disposition of the pistils;

FIG. 7, a specimen of a petal from the outer periphery of the flower, outside view;

FIG. 8, a specimen of a petal from the outer periphery of the flower, inside view;

FIG. 9, a specimen of receptacle, from which the stamens and pistils have been taken out;

FIG. 10, a portion of flower-bearing branch;

FIG. 11, a portion of a main branch;

FIG. 12, a specimen of leaf with 3 folioles, upper surface;

FIG. 13, a specimen of leaf with 5 folioles, upper surface;

FIG. 14, a specimen of leaf with 7 folioles, under surface.

DETAILED DESCRIPTION OF DISCLOSURE

The chart used for the identification of the colors is that of the Royal Horticultural Society (R.H.S. Color Chart). The terminology preceding the numbered references, proper to this chart, has been added to designate, in common terms, the corresponding colors.

Class: Hybrid tea.

Plant:

*Development.*—On plants pruned to about Om. 85, the length of the flowering stems is between 50 and 80 cms.

*Habit.*—Erect.

Branches:

*Color.*—Young stems: Before buds are formed, they are reddish purple (sunny side) and light green (shaded side); as and when buds are formed the reddish purple color tends to disappear and to turn to light green. Mature wood: Medium green 137/C (green group).

*Prickles.*—Shape: Upper edge: Straight. Under edge: Concave. Base: Obovate, narrow. Size: Medium—they are narrow and tapered (length 10/11 mms.). Quantity: Average. Color: On young stems: Reddish purple. On mature wood: In succession light bronze, somewhat havana and reddish (common terms).

Leaves:

*Stipules.*—Adnate, pectinate, narrow and linear.

*Petiole.*—Obverse: The inside and edges of the rib are more or less reddish brown in the young foliage, bronze green, then normal green in the adult foliage. The edges are generally slightly, to very slightly glandular. Reverse: Light green—with a few small prickles, hooked and greenish straw color.

It forms, with the stem, an angle between 45 and 90°.

*Folioles.*—Number: 3–5–7. Shape: On a standard-model leaf on the average ⅓ of a flower-bearing branch (first pair starting from the top). Base: Rounded, asymmetrical. Top: Fairly wide, symmetrical. Shape as a whole: Elliptical, sometimes spear-head shaped. Teeth: Single—coarse. Texture: Medium firm to leathery. General effect: Fairly ample and dense foliage—shiny. Color—Young foliage. Upper surface: Medium green, slightly darker than 137/A (green group). Under surface: Light green, between 138/B and 138/C (green group). Adult foliage. Upper surface: Medium green darker than 137/A (green group). Under surface: Light green, between 138/B and 138/C (green group).

Inflorescence:

*Number of flowers.*—One per stem. It is to be noted that, when forcing, the 2 or 3 first stipular eyes of the flower-bearing branches sometimes develop very rapidly and form tigellas going very much beyond the bud; hence, it is necessary to nip off some buds.

*Peduncle.*—Erect—rigid—with slightly thorny base—light green—tinted with reddish brown near the receptacle. Length: From 9 to 11 cms.

*Sepals.*—Downy—greenish white inside—light green and smooth outside—narrow and tapered—a few appendages on the edge.

*Bud.*—Shape—before the opening of the sepals: Pointed, tapered. When 1st petal opens: Pointed, fairly elongated, funnel-shaped tip.

*Length.*—32 mms. outside of the calyx, at the opening of the 1st petal.

*Size.*—Medium.

*Color.*—When opening: Inside: Vermilion red 44/A (red group). Outside: Blood red 45/D (red group) more or less spotted with blackish purple (common terms).

*Flower.*—Form: At the opening, the center petals are level with those of the outer periphery; then they open progressively giving the flower a full, flat shape; afterwards as a hollow cup; outer petals folded in a point, folded overlapping petals on the inner periphery; visible stamens.

*Double flower.*—Diameter: 10/12 cms. Color—When opening. Inside: Vermilion red 44/B (red group) flushed with tone 44/A. Outside: Blood red 45/D (red group) lightly shaded with 45/C. During the course of opening: Inside: Light vermilion red 44/C in the center, shaded with 44/B towards the edge (red group). Outside: Blood red 45/C (red group) shaded with cardinal red 53/B (red group) near the center of the flower. When fully open: Inside: Blood red 45/D (red group) lightened with 45/C. Outside: Blood red 45/D shaded with 53/D (red group).

It is to be noted that the 2 or 3 petals making up the outside of the flower usually have a few blackish purple spots, toning down to reddish brown (common terms) especially round and along the median rib, as well as at the tips of the petals.

Fragrance: Without.

Lasting quality when cut: Long.

Corolla:

*Petals.*—Texture: Very firm—the unguis is yellowish at the joining point, with a slight white aureole, more pronounced on the inside than on the outside, and itself bordered with a very succinct fuchsine pink.

*Shape.*—Round, flat—the tips and lateral edges are more or less reflexed—those of the outer periphery are folded in a point—the extreme point is needle-like.

*Number.*—35 on an average.

The petals drop off cleanly.

*Stamens.*—Number: 150 on an average. Anthers: Normal—the inside and outside of the cells are slightly spotted with fuchsine (common term); the edges are yellow. Filaments: Uneven in length, rather short—red with yellow base.

*Pistils.*—Number: 100 on an average. Stigmas: Light yellow—above the orifice of the receptacle and distinctly above the level of the anthers. Styles: Free—downy—greenish yellow at base, then slightly carmine up to the stigmas.

*Receptacle.*—Light green—smooth—lengthwise it is narrow and in the shape of a pitcher.

Development:

*Vegetation.*—Very vigorous.

*Aptitude to forcing.*—Very great.

*Resistance to diseases.*—No special aptitude.

We claim:

1. A new and distinct variety of rose plant of the hybrid tea class substantially as illustrated and described, distinguished as to novelty, from the physical point of view, the plant, with medium green adult foliage, is erect, the flower is double, light vermilion red inside, blood red outside, the petals are very firm and have a yellowish unguis with a white aureole, itself bordered with a succcinct fuchsine pink halo;

from the biological point of view, this rose-plant grows very vigorously, shows great aptitude to forcing, is not specially sensitive to diseases, its flowers last a long time when cut, and the petals drop off cleanly.

No references cited.

ROBERT E. BAGWILL, Primary Examiner